US011793451B2

(12) United States Patent
Lewis et al.

(10) Patent No.: US 11,793,451 B2
(45) Date of Patent: Oct. 24, 2023

(54) INTERFACE AND ANALYSIS TECHNIQUES FOR CUSTOMIZED SKIN CARE REGIMEN BASED ON SKIN DIAGNOSTICS

(71) Applicant: L'Oreal, Paris (FR)

(72) Inventors: Jason Lewis, Seattle, WA (US); Kathy Chi-Thurber, Seattle, WA (US)

(73) Assignee: L'OREAL, Paris (FR)

( * ) Notice: Subject to any disclaimer, the term of this patent is extended or adjusted under 35 U.S.C. 154(b) by 294 days.

(21) Appl. No.: 16/945,633

(22) Filed: Jul. 31, 2020

(65) Prior Publication Data

US 2022/0031229 A1 Feb. 3, 2022

(51) Int. Cl.
| *A61B 5/00*  | (2006.01) |
| *G16H 40/67* | (2018.01) |
| *A45D 44/00* | (2006.01) |
| *G16H 20/00* | (2018.01) |

(52) U.S. Cl.
CPC .............. *A61B 5/442* (2013.01); *A45D 44/00* (2013.01); *A61B 5/0077* (2013.01); *A61B 5/7475* (2013.01); *G16H 20/00* (2018.01); *G16H 40/67* (2018.01); *A45D 2044/007* (2013.01)

(58) Field of Classification Search
None
See application file for complete search history.

(56) References Cited

U.S. PATENT DOCUMENTS 9,760,935 B2    9/2017  Aarabi
11,178,956 B1 * 11/2021 Prout ................... A45D 44/005

| 2003/0064350 | A1 * | 4/2003  | Rubinstenn ............ A61B 5/444 |
|              |      |         |                            434/99 |
| 2011/0301441 | A1 * | 12/2011 | Bandic ................. A61B 5/4875 |
|              |      |         |                           600/306 |
| 2012/0299945 | A1   | 11/2012 | Aarabi |
| 2013/0268395 | A1 * | 10/2013 | Sandow ................. G06Q 30/02 |
|              |      |         |                          705/26.7 |
| 2015/0339757 | A1 * | 11/2015 | Aarabi ............... G06Q 30/0631 |
|              |      |         |                          705/26.7 |

(Continued)

FOREIGN PATENT DOCUMENTS

| WO | 2018/182985 A1 | 10/2018 |
| WO | 2020/113326 A1 | 6/2020  |

*Primary Examiner* — Matthew Kremer
*Assistant Examiner* — Matthew Eric Ogles
(74) *Attorney, Agent, or Firm* — CHRISTENSEN O'CONNOR JOHNSON KINDNESS PLLC

(57) ABSTRACT

A computer system generates a computer-guided personal care routine based at least in part on a digital model of a user's face. In an embodiment, a computer system generates the model based on one or more images or scans of the user's face, and generates a computer-guided personal care routine based on the model, environmental data (e.g., temperature data, humidity data, pollution data, UV radiation data), and user data. In an embodiment, a routine generated on this basis includes multiple steps to be carried out using a computer-controlled skin care device as well as user prompts related to execution of such steps that are configured to be presented in a user interface. In an embodiment, the computer-guided routine includes one or more operational settings (e.g., brush head speed, cleansing duration) for the computer-controlled skin care device that are automatically set at appropriate times according to the generated routine.

20 Claims, 15 Drawing Sheets

(56) References Cited

U.S. PATENT DOCUMENTS

| | | | |
|---|---|---|---|
| 2017/0270593 A1* | 9/2017 | Sherman | G06V 40/171 |
| 2017/0340267 A1* | 11/2017 | Shen | G16H 40/67 |
| 2018/0357761 A1* | 12/2018 | Shen | A61B 5/441 |
| 2021/0027897 A1* | 1/2021 | Rasochova | A61B 5/0077 |
| 2021/0182705 A1* | 6/2021 | Bates | G06N 20/00 |
| 2021/0289128 A1* | 9/2021 | Dong | H04N 23/676 |
| 2022/0225927 A1* | 7/2022 | Yoo | A61B 5/441 |

* cited by examiner

SKIN QUIZ

Select your focus areas

☐ Forehead

☑ Nose

☐ Chin

☑ Cheeks

I'm done. Lets go.

*FIG. 9*

INTERFACE AND ANALYSIS TECHNIQUES FOR CUSTOMIZED SKIN CARE REGIMEN BASED ON SKIN DIAGNOSTICS

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure relates to generating custom personal care regimens based on skin diagnostics. In described embodiments, a computer system generates computer-guided personal care routines for smart personal care devices based on digital models of users' skin.

In one aspect, a computer system performs operations comprising obtaining a digital model of a face of a live human subject; obtaining user data associated with the live human subject; and generating a computer-guided skin care routine based at least in part on the digital model of the face of the live human subject, the environmental data, and the user data. In an embodiment, the computer-guided skin care routine comprises one or more operational settings (e.g., brush speed or intensity, duration of cleansing) for a computer-controlled skin care device. In another embodiment, the computer-guided skin care routine includes a product recommendation (e.g., a recommended device attachment, skin cleanser, eye cream, sunscreen, makeup product, etc.) presented via a user interface. In another embodiment, the computer-guided skin care routine includes a self-care recommendation (e.g., a hydration or moisturizing recommendation, a UV protection recommendation, a stress-reduction recommendation, a sleep recommendation, etc.) presented via a user interface.

In an embodiment, the digital model is based on one or more digital scans of the face and includes a plurality of skin features to be targeted in a skin care routine, such as one or more blemishes, areas of hyper-pigmentation, texture, or wrinkles, or a combination thereof.

In an embodiment, the computer system obtains environmental data (e.g., temperature data, humidity data, pollution data, or UV radiation data, or a combination thereof) associated with the environment of the live human subject, and the computer-guided skin care routine is further based on the environmental data. The environmental data is obtained from a remote computer system or one or more environmental sensors or a combination thereof. In some embodiments, the environmental sensors are integrated in a skin care device or in a smart phone or other computing device in communication with a skin care device.

In some embodiments, a user interface includes one or more user interface elements for providing feedback on or modifying the computer-guided skin care routine or other data on which the routine is based, such as user preferences (e.g., an age target, device preferences). In such an embodiment, operations performed by the computer system further include obtaining user feedback (e.g., a satisfaction score or rating, an adjusted age target or skin care goal, etc.) relating to the computer-guided skin care routine via the user interface and/or modifying the computer-guided skin care routine.

Computer-implemented methods, computer-readable media, computing devices and computer systems are disclosed.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 7-9 are screenshot diagrams of illustrative questionnaire screens for obtaining user data, in accordance with a described embodiment;

DETAILED DESCRIPTION

Figure 1:
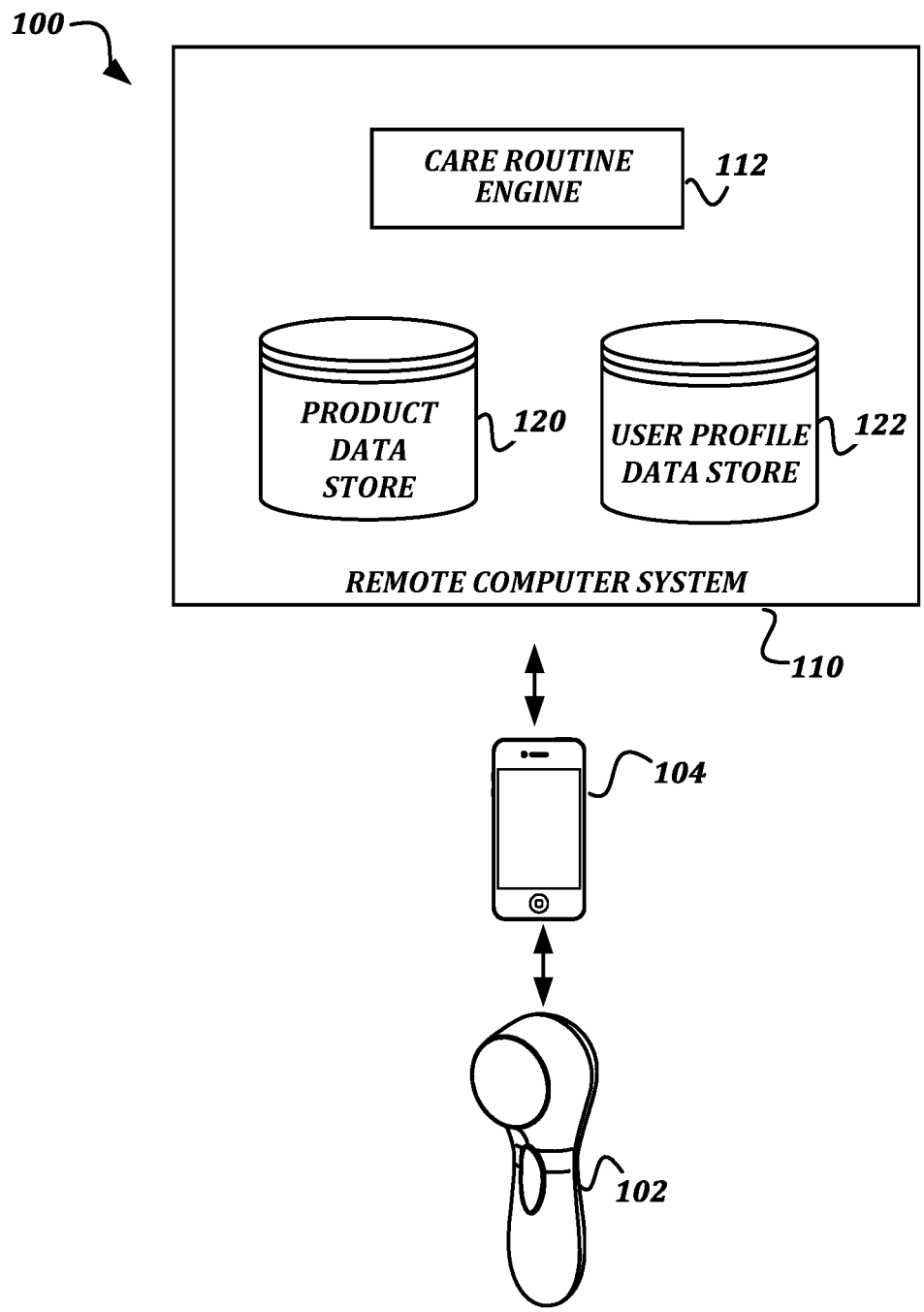
FIG. 1 is a schematic diagram that provides a high-level overview of a system that includes a skin care device according to aspects of the present disclosure.

Although a wide variety of personal care products and personal care devices are available today, discovering the best way to use such products or devices effectively is often a matter of trial and error. Although consumers may use internet search engines to find relevant information about the capabilities of such devices, consumers are often unable to configure or use those devices in optimal ways based on such information. Furthermore, as such devices become more complex, and include more programmable and Internet-connected features, the act of configuring and using such devices also becomes more complex, especially for ordinary consumers. This leaves consumers unable to benefit from all the ways their devices could be configured and used.

Embodiments described herein provide technical solutions to one or more of the technical problems described above, or other technical problems.

In embodiments disclosed herein, a computer system generates a computer-guided skin care routine based at least in part on a digital model of a user's face. In an embodiment, a computer system obtains a digital scan of a user's face along with other inputs such as environmental data associated with the environment of the user and user data associated with the user. The system uses this data to generate a computer-guided skin care routine. In an embodiment, the computer system includes one or more server computers, which obtains the digital scan from a client device, such as a smart phone with an integrated digital camera, and generates a digital model of the user's face based on the digital scan.

In an embodiment, the computer-guided skin care routine includes user prompts, recommendations, or other output presented to a user via video, audio, or other output via a client computing device or via a human-machine interface integrated in a skin care device. In an embodiment, the generated routine includes steps of using the skin care device that are adapted to the user's face, the user's environment, and other information related to the user, such as the user's age, preferences, and skin care goals. The generated routine may be a new routine or a modified version of a previously existing routine. For example, if a face scan reveals a new blemish that was not present when an existing routine was developed, the generated routine may be adapted to provide an additional step for treating the blemish. As another example, an existing care routine may be adjusted to account for new environmental data (e.g., decreased humidity, increased temperature, increased pollution, etc.). The generated routine may be based on criteria such as characteristics of a skin care device (e.g., available settings or attachments), previous outcomes, user preferences or behaviors, time of day, current month/season of the year, day of the week, or the like.

A wide variety of operational parameters for skin care devices may be set in particular ways in programmed or guided care routines. For example, adjustable parameters for powered skin brushes or massagers may include adjustable power settings, timers, speed settings (e.g., rotation or oscillation speed for a brush head), haptic feedback parameters, or other parameters or combinations of parameters. These parameters may be automatically set and/or adjusted over time in a computer-guided skin care routine.

In an embodiment, the smart skin care device provides cues or prompts to users during a care routine, such as audio cues, haptic cues, or visual cues, which may be used to guide a user through different stages of the care routine, such as moving a skin care device to different skin areas, changing speeds, changing cleansing modes, and the like. In such embodiments, the smart skin care device may include speakers, displays, lights, or haptic electronics such as tactile sensors or vibrating actuators. The guided care routine functionality of smart skin care device may be activated in various ways, such as by a hardware button press (e.g., an on/off switch or a dedicated button for activating a care routine), by a voice command, or in some other way.

In an embodiment, a smart skin care device further includes wireless communication circuitry, such as a wireless transceiver for Wi-Fi communication. In such an embodiment, the smart personal care device may access a voice-interface service via wireless communication circuitry from a remote computer system. In another embodiment, the smart personal care device further includes Bluetooth or near-field communication (NFC) circuitry, either in place of or in addition to Wi-Fi communication circuitry. In such an embodiment, the smart skin care device may communicate with an external client computing device, such as a smart phone or tablet computer, which may in turn access a voice-interface service via its own communication circuitry from a remote computer system. In another embodiment, the smart skin care device includes circuitry for communicating with a smart speaker, such as an Amazon Echo or Google Home device, which may include its own voice-interface service or communicate with a remote computer system to access voice-interface services.

In an embodiment, user data may be obtained from user profiles, which may be used to store system preferences, social network account or contact information, product/service provider ratings or preferences, location information, questionnaire answers, information from connected devices (e.g., smart personal care devices such as hair dryers, powered skin brushes, or the like), or other information.

In an embodiment, a smart skin care device includes sensors for detecting characteristics of the physical environment (e.g., humidity, temperature, ambient light levels, etc.) of the device during a care routine. Alternatively, the system can obtain data from remote sensors that may not be included in the skin care device itself. The information generated by such sensors can be used by the skin care device (or computer systems that may be in communication with the device) in order to help guide the user through the routine or to make adjustments for better results.

Information obtained from devices may be used to guide custom product or care routine selections, or for other purposes. Such information may include device identification information, configuration information, usage information (e.g., how often a device is used, duration of use, time of day, etc.), sensor information (e.g., measurements of environmental conditions such as temperature, humidity, pollution levels, UV radiation levels, etc., or skin conditions such as pH levels), location information, combinations of such information, or other information. Sensor information may be provided via sensor-enabled or connected Internet-of-Things (IoT) devices. Such devices may include weather stations, mobile computing devices, and the like.

FIG. 1 is a block diagram that illustrates a system in which various aspects of the present disclosure may be implemented. As shown in FIG. 1, the system 100 includes a skin care device 102 (in the illustrated example, a powered skin brush or massager) with wireless communication circuitry. The skin care device 102 may send and/or receive information (e.g., usage data, device identification/configuration data, environmental data, or the like) to and/or from a remote computer system 110, either directly or via one or more intermediary devices such as client computing device 104, as described below.

In the illustrative arrangement depicted in FIG. 1, a client computing device 104 connects to the remote computer system 110, which may generate custom content for a user, such as computer-guided skin care routines, product recommendations, or settings or parameters for operation of a personal care device. In examples described herein, the personal care device is a skin care device 102, as described in further detail below. In an embodiment, a custom care routine for a skin cleansing device includes a defined pattern of skin areas to be cleansed during the routine, time durations for each skin area, and brush head speeds or cleansing modes for each skin area. In an embodiment, custom routines or device settings may be uploaded to the client computing device 104 for subsequent transmission to the skin care device 102. Skin care devices 102 may also include or communicate with environmental sensors and/or other computing devices. Illustrative components of the remote computer system 110 and the skin care device 102 are described below.

The client computing device 104 may be used by a consumer, skin care professional, or other entities to interact with other components of the system 100, such as the remote computer system 110 or skin care device 102. In an embodiment, the client computing device 104 is a mobile computing device such as a smart phone or a tablet computing device. However, any other suitable type of computing device capable of communicating via the network and presenting a user interface may be used, including but not limited to a desktop computing device, a laptop computing device, a smart speaker, or a smart watch (or combinations of such devices).

Illustrative components and functionality of the remote computer system 110 will now be described. The remote computer system 110 includes one or more server computers that implement the illustrated components, e.g., in a cloud computing arrangement. As illustrated in FIG. 1, the remote computer system 110 includes a care routine engine 112, a product data store 120, and a user profile data store 122. The care routine engine 112 generates guided care routine information, which can then be transmitted to, e.g., the client computing device 104 and/or the skin care device 102. The guided care routine information may include, for example, programmatic care routine instructions for programming or configuring the skin care device 102 in a particular way, product recommendations, tutorials, or other information.

In an embodiment, the care routine engine 112 generates guided care routine information based on information received from the product data store 120 along with user information from the user profile data store 122, the skin care device 102, the client computing device 104, or a combination thereof or from some other source or combination of sources. The care routine engine 112 may, for example, receive a request for an updated care routine from the skin care device 102 or the client computing device 104, obtain information from the product data store 120 (e.g., available settings and configurations for the skin care device 102, available attachments, etc.), the user profile data store 122 (e.g., users' answers to questions about themselves, device usage data, preferred care routines, location, age, products used, etc.), or the client computing device 104 (e.g., information describing the user's current location, satisfaction with previous routines (indicated by e.g., star rating or number rating), current mood/stress level, etc.), and use this information to perform further processing. The care routine engine 112 may use the information it obtains to, e.g., generate a new routine or update a previously defined routine.

The care routine engine 112 may employ machine learning or artificial intelligence techniques (e.g., template matching, feature extraction and matching, classification, artificial neural networks, deep learning architectures, genetic algorithms, or the like). In an embodiment, machine learning techniques are used to analyze data such as a digital scan of a user's face, environmental data, and user data, and create or revise care routines, product recommendations, or other content based on this data. For example, to generate a custom care routine, the care routine engine 112 may analyze digital scans to measure or map wrinkles, pigmentation, skin texture, etc., of the user's skin. In such a scenario, the care routine engine 112 may use such information to recommend, generate or modify a particular care routine that suits the particular features of the user's skin.

In an embodiment, location information obtained by a skin care device or a client computing device may be used to look up and obtain other information from other computing devices or systems, which may be relevant to a care routine. For example, a client computing device 104 may provide location information to a remote computer system 110, which may in turn obtain current environmental data (e.g., weather information, pollution information, UV radiation information, etc.) for the respective location. The remote computer system 110 may then use the environmental data to generate or modify a care routine. In an illustrative scenario, the remote computer system 110 uses location information to determine that the user is in a hot, polluted city; and generates or modifies a care routine to account for this environment.

In an embodiment, information is stored, transmitted, and shared within the system 100 in a secure and reliable manner. For example, secure connections are established between client computing devices and skin care devices, between client computing devices and server systems, or any other set of communicating devices. Users may be securely reminded of care routine events, environment alerts (e.g., temperature, humidity, pollution, or UV radiation warnings), product expirations, and the like via push notifications to a client application, email, instant messaging, or some other communication channel.

Figure 2:
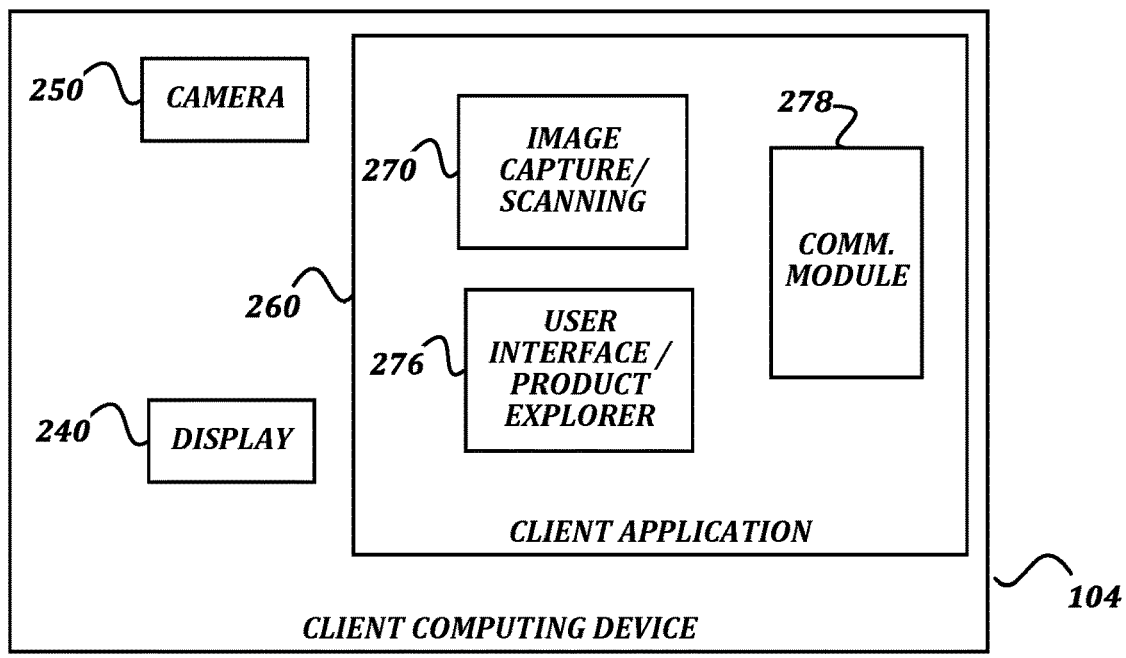
FIG. 2 is a block diagram that illustrates an example embodiment of a client computing device according to aspects of the present disclosure.

FIG. 2 is a block diagram that illustrates an example embodiment of a client computing device 104 according to various aspects of the present disclosure. FIG. 2 depicts a non-limiting example of client computing device features and configurations; many other features and configurations are possible within the scope of the present disclosure.

In the example shown in FIG. 2, the client computing device 104 includes a camera 250 and a client application 260. The client application 260 includes a user interface 276, which may include interactive functionality such as data collection or questionnaire elements, tools for entering or editing user preferences, care routine editing tools, tutorials, virtual "try-on" functionality for virtually testing different products or cosmetics, or other elements. Visual elements of the user interface 276 are presented on a display 240, such as a touchscreen display. Customized content, such as computer-guided skin care routines, may be obtained by the client computing device 104 (e.g., from the remote computer system 110) and presented via the user interface 276. Details of an illustrative user interface are described below with reference to FIGS. 5-14.

In an embodiment, the client application 260 also includes an image capture/scanning module 270, which is configured to capture and process digital images (e.g., color images, depth images, etc.) or scans on which digital models described herein are based. In an embodiment, the digital images or scans are transmitted to remote computer system 110 or some other external computer system where the digital skin models are generated. Alternatively, the digital models are generated at the client computing device 104 or at some other location. In an embodiment, the digital models include 3D topology and texture information, which can be used for reproducing an accurate representation of the user's facial structure and overall appearance, as well as for skin diagnostics (e.g., to detect blemishes, areas of hyper-pigmentation, visible pores, etc.). In an embodiment, the user interface 276 includes user interface elements to assist in accurately capturing the digital images or scans on which these digital skin models are based.

In an embodiment, a communication module 278 of the client application 260 is used to prepare information for transmission to, or to receive and interpret information from other devices or systems, such as the remote computer system 110 or a skin care device 102. Such information may include captured digital images, scans, or video, skin care device settings, custom care routines, user preferences, user identifiers, device identifiers, or the like.

Other features of client computing devices are not shown in FIG. 2 for ease of illustration. A description of illustrative computing devices is provided below with reference to FIG. 15.

Figure 3:
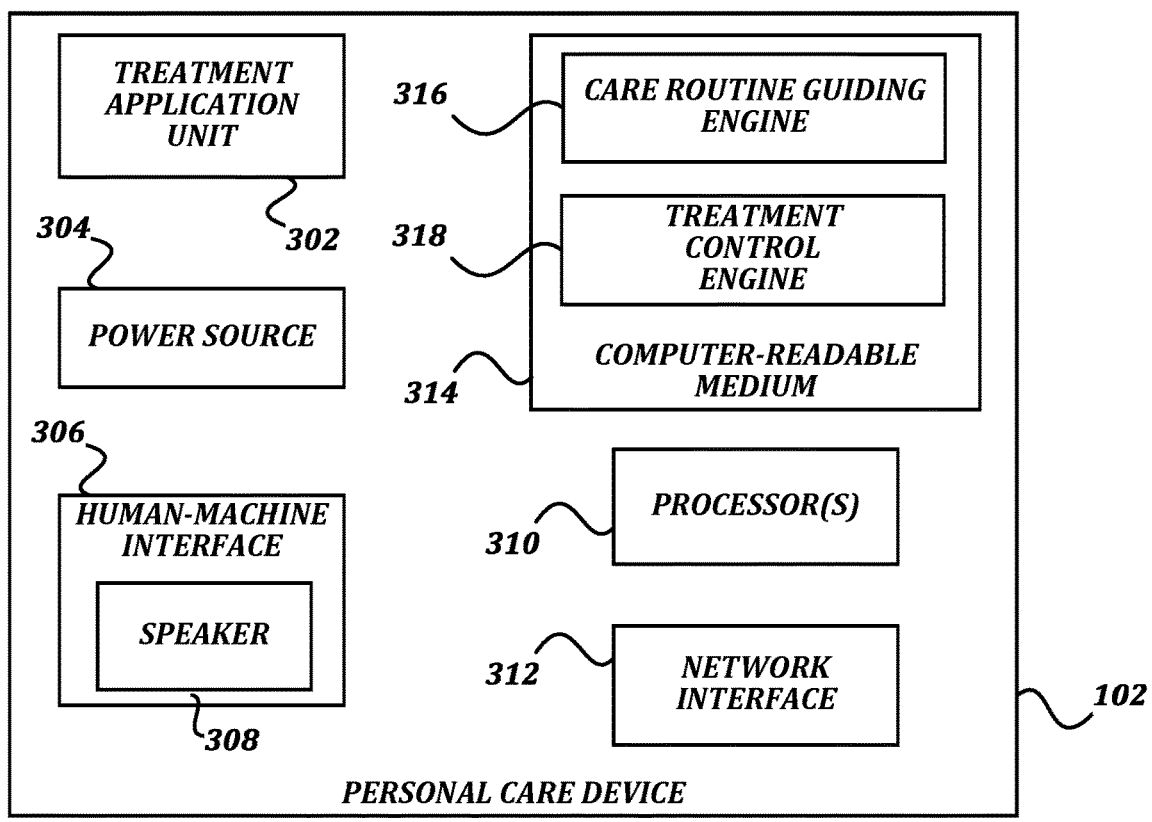
FIG. 3 is a block diagram that illustrates an example embodiment of a skin care device according to aspects of the present disclosure.

FIG. 3 is a block diagram that illustrates components included in an example embodiment of a skin care device according to various aspects of the present disclosure. FIG. 3 depicts a non-limiting example of skin care device features and configurations; many other features and configurations are possible within the scope of the present disclosure.

In the example shown in FIG. 3, the skin care device 102 includes a treatment application unit 302 configured to apply a treatment to a user, a power source 304, a human-machine interface device 306, a processor 310, a network interface 312, and a computer-readable medium 314. One non-limiting example of a skin care device 102 is a powered facial cleansing brush with a brush head that oscillates, rotates, or otherwise moves in order to perform a scrubbing action. Other non-limiting examples of skin care devices 102 include a massaging device or a phototherapy device that may be used to expose skin to light (e.g., at a particular wavelength and/or at a particular time duration) to achieve therapeutic benefits.

In an embodiment, the treatment application unit 302 includes one or more devices that collectively apply a treatment to a user. For example, if the skin care device 102 is a powered skin brush, the treatment application unit 302 may include a drive motor, an armature coupled to the drive motor that accepts a detachable brush head, and the brush head itself. As another example, if the skin care device 102 is a handheld phototherapy device, the treatment application unit 302 may include one or more light-emitting diodes (LEDs) or other light-emitting devices that emit light of suitable wavelengths and intensity for phototherapy applications.

In an embodiment, the power source 304 is a rechargeable battery that provides power to the treatment application unit 302 for operation. The power source 304 also may also provide power for operation to the other components of the skin care device 102. In other embodiments, instead of a battery, the skin care device 102 may be coupled to an external power source, such as an electrical outlet.

The human-machine interface (HMI) 306 may include any type of device capable of receiving user input or generating output for presentation to a user. In an embodiment, the HMI 306 includes a speaker 308 to allow the skin care device 102 to present audio content (e.g., care-routine cues in the form of synthesized or recorded speech, tones, etc.) and/or a microphone receive audio input, such as voice commands from a user. In addition to voice cues, the speaker 308 may present other output to accompany the care routine such as music, calming nature sounds, or the like. Other non-limiting examples of possible components of the HMI 306 include a push-button switch, a toggle switch, a capacitive switch, a rotary switch, a slide switch, a rocker switch, and a touch screen.

The processor 310 is configured to execute computer-executable instructions stored on the computer-readable medium 314. In an embodiment, the processor 310 is configured to receive and transmit signals to and/or from other components of the skin care device 102 via a communication bus or other circuitry. The network interface 312 is configured to transmit and receive signals to and from the client computing device 104 (or other computing devices) on behalf of the processor 310. The network interface 312 may implement any suitable communication technology, including but not limited to short-range wireless technologies such as Bluetooth®, infrared, near-field communication, and Wi-Fi; long-range wireless technologies such as WiMAX (Worldwide Interoperability for Microwave Access), 2G, 3G, 4G, LTE (Long Term Evolution), and 5G; and wired technologies such as USB (Universal Serial Bus), FireWire, and Ethernet. The computer-readable medium 314 is any type of computer-readable medium on which computer-executable instructions may be stored, including but not limited to a flash memory, a ROM, an EPROM (erasable programmable read-only memory), an EEPROM (electrically erasable programmable read-only memory), and an FPGA (field programmable gate array). The computer-readable medium 314 and the processor 310 may be combined into a single device, such as an ASIC (application-specific integrated circuit), or the computer-readable medium 314 may include a cache memory, a register, or another component of the processor 310.

In the illustrated embodiment, the computer-readable medium 314 has computer-executable instructions stored thereon that, in response to execution by one or more processors 310, cause the skin care device 102 to implement a care routine guiding engine 316 and a treatment control engine 318. The treatment control engine 318 controls one or more aspects of the skin care device 102 in a care routine, as described above. In an embodiment, the care routine is generated and/or modified by the care routine engine 112, as described above. In an embodiment, the treatment control engine 318 adjusts settings or configurations for the skin care device 102, which may be generated and/or modified by the care routine engine 312, as described above. In an embodiment, the treatment control engine 318 controls basic functions such as turning the treatment application unit on or off, controlling brush head speed, or the like. In an embodiment, the treatment control engine 318 detects input from of the HMI 306, and activates the treatment application unit 302 or modifies a function of the skin care device 102 in response to the input. The treatment control engine 318 may then detect a subsequent input from the HMI 306 and deactivate the treatment application unit 302 or make further adjustments to the function of the skin care device 102 in response, or may allow the treatment application unit 302 to operate for a predetermined amount of time before automatically deactivating the treatment application unit 302.

In an embodiment, the care routine guiding engine 316 controls presentation of care routine cues, such as by causing audio cues to be output by the speaker 308 in order to guide a user's actions during a care routine. In an embodiment, the care routine guiding engine 316 collects data such as data describing execution of care routines, environmental data, or other data. In an embodiment, data collected by the care routine guiding engine 316 is transmitted via the network interface 312 to the remote computer system 110 (e.g., via the client computing device 104 or directly) for storage (e.g., in the product data store 120 or user profile data store 122) or for further processing (e.g., to update a computer-guided care routine, adjusting skin care device settings, etc.). In an embodiment, the collected data is used along with face scan data to perform such updates or adjustments.

In an embodiment, the processor(s) 310 and the computer-readable medium 314 provide circuitry that may be collectively referred to as a skin care unit of the skin care device 102. In an embodiment, the skin care unit is operably coupled to the HMI 306 and to the treatment application unit 302 and includes circuitry for controlling the treatment application unit 302. In an embodiment, the skin care unit includes circuitry for presenting voice cues, visual cues, or other cues via the HMI in a computer-guided care routine to guide user operation of a skin care device. Alternatively, the skin care device 102 may include different circuitry, or the circuitry may be implemented in some other way.

The devices shown in FIGS. 1-3 or other devices used in described embodiments may communicate with each other via a network (not shown), which may include any suitable communication technology including but not limited to wired technologies such as DSL (digital subscriber line), Ethernet, fiber optic, USB, and Firewire; wireless technologies such as WiFi, WiMAX, 3G, 4G, LTE, 5G, and Bluetooth®; and the Internet. In general, communication between the components of the systems in FIG. 1 or other computing devices may occur directly or through intermediate devices.

Many alternatives to the arrangement disclosed and described with reference to FIGS. 1-3 are possible. For example, functionality described as being implemented in multiple components may instead be consolidated into a single component, or functionality described as being implemented in a single component may be implemented in multiple illustrated components, or in other components that are not shown in FIGS. 1-3. As another example, devices in FIGS. 1-3 that are illustrated as including particular components may instead include more components, fewer components, or different components without departing from the scope of described embodiments.

Within components of the system depicting in FIG. 1 or devices depicted in FIGS. 2 and 3 or by components of such systems and devices working in combination, numerous technical benefits are achieved. For example, the ability to automatically generate or modify care routines based on digital scans of a user's face in combination with additional data such as user data and environmental data overcomes technical limitations of prior technologies that depended on user's abilities to configure their own devices. As another example, the system 100 allows some aspects of the process to be conducted independently by skin care devices or client computing devices, while moving other processing burdens to the remote computer system 110 (which may be a relatively high-powered and reliable computing system), thus improving performance and preserving battery life for functionality provided by skin care devices or client computing devices.

In general, the word "engine," as used herein, refers to logic embodied in hardware or software instructions written in a programming language, such as C, C++, COBOL, JAVA™, PHP, Perk HTML, CSS, JavaScript, VB Script, ASPX, Microsoft .NET™, and/or the like. An engine may be compiled into executable programs or written in interpreted programming languages. Software engines may be callable from other engines or from themselves. Generally, the engines described herein refer to logical modules that can be merged with other engines or divided into sub-engines. The engines can be stored in any type of computer-readable medium or computer storage device and be stored on and executed by one or more general purpose computers, thus creating a special purpose computer configured to provide the engine or the functionality thereof.

As understood by one of ordinary skill in the art, a "data store" as described herein may be any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, as described further below. One of ordinary skill in the art will recognize that separate data stores described herein may be combined into a single data store, and/or a single data store described herein may be separated into multiple data stores, without departing from the scope of the present disclosure.

Figure 4:
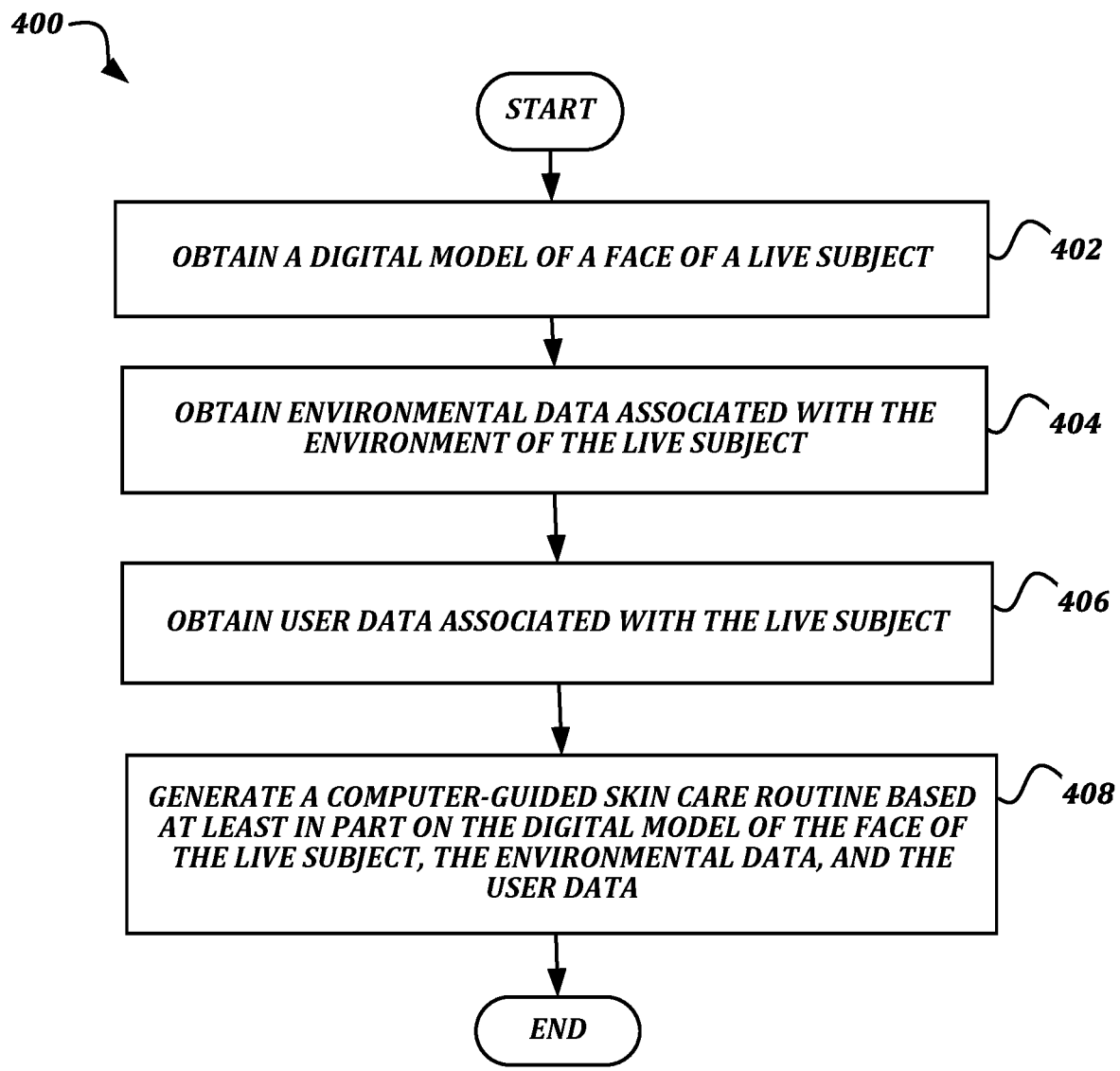
FIG. 4 is a flowchart that illustrates an example embodiment of a method of generating a computer-guided skin care routine based at least part on a digital model of the face of the live human subject according to aspects of the present disclosure.

FIG. 4 is a flowchart that illustrates an example embodiment of a method of generating a computer-guided skin care routine based at least part on a digital model of the face of the live human subject. As illustrated, the method 400 is implemented by a computer system. The method 400 may be implemented by a server computer system including features of the remote computer system 110, by a client computing device, by a skin care device 102, or by some other computing device or system.

From a start block, the method 400 proceeds to block 402, where the computer system obtains a digital model (e.g., based on one or more digital images or scans) of the face of a live human subject. In an embodiment, the computer system includes a server computer that obtains one or more digital images or scans from a client device, such as a smart phone with an integrated digital camera. In such an embodiment, these images or scans are captured by the client device and uploaded to the server computer, which generates the digital model. In an embodiment, the digital model includes a highly accurate model of facial characteristics and features, including lip and eye edges, iris size and location, skin features including spots, texture, and wrinkles, and the like. It will be understood that the skin characteristics and features described herein are only examples, and that other characteristics or features or combinations of such characteristics or features are also desirable and are within the scope of the present disclosure. In an embodiment, the source images are captured and the digital models are generated using Modiface software available from Modiface, Inc.

The method 400 proceeds to an optional step 404, where the computer system obtains environmental data associated with the environment of the live human subject. In an embodiment, the computer system obtains environmental data from environmental sensors at the user's location (e.g., via sensors embedded in a client computing device or skin care device used by the user). Alternatively, the computer system obtains environmental data from another device or computer system. In an embodiment, the computer system determines the user's approximate location (e.g., as reported by the user or a location-aware computing device) and requests environmental data related to that location from a computer system dedicated to providing weather or environmental data. The method proceeds to step 406, where the computer system obtains user data associated with the live subject. In an embodiment, user data may be obtained from user profiles stored in user profile data store 122. Alternatively, user data may be obtained directly from client computing device 104, skin care device 102, or from some other source. In an embodiment, the user data includes system or device preferences, device usage information, social network account or contact information, product/service provider ratings or preferences, location information, questionnaire answers, or a combination thereof, or other information. In an embodiment, the user data includes an age target, which a user may set to adjust a skin care routine to a particular target age. For example, a 50-year-old user may select an age target of 45, which causes a moderate skin care routine to be generated to achieve a moderate difference in appearance. Alternatively, the 50-year-old user selects an age target of 40, which causes a more intensive skin care routine to be generated.

The method proceeds to step 408, where the computer system generates a computer-guided skin care routine based at least part on the digital model of the face of the live human subject, the environmental data, and the user data. In an embodiment, the care routine engine 112 of remote computer system 110 obtains these inputs and generates the computer-guided skin care routine. Alternatively, the routine is generated based on different combinations of inputs. For example, where environmental data is not obtained or not available, the computer system generates a computer-guided skin care routine based on the digital model of the face and the user data.

In an embodiment, some aspects of the computer-guided skin care routine, such as user prompts, are configured to be presented in a user interface. In an embodiment, the computer-guided care routine includes automatically activating one or more voice cues or other prompts stored in memory of the skin care device. Alternatively, the routine is presented via a display or some other modality. The computer-guided care routine may be controlled by, e.g., the care routine guiding engine 316 of the skin care device 102.

In an embodiment, a user interface (UI) includes one or more user interface elements for providing or modifying user data, capturing face images or scans, or otherwise obtaining or modifying data on which computer-guided skin care routines may be based, and/or for providing feedback on or modifying a previously generated computer-guided skin care routine. In such an embodiment, operations performed by the computer system further include obtaining user feedback (e.g., a satisfaction score or rating, an adjusted age target or skin care goal, etc.) relating to the computer-guided skin care routine via the UI and/or modifying the computer-guided skin care routine.

Aspects of an illustrative UI to collect information and provide user feedback and control for generated computer-guided skin care routines will now be described with reference to FIGS. 5-14. The UI described with reference to FIGS. 5-14 is only illustrative, and it will be understood that many alternative UI features, as well as alternative techniques for generating computer-guided skin care routines, may be developed in accordance with the present disclosure.

Figure 5:
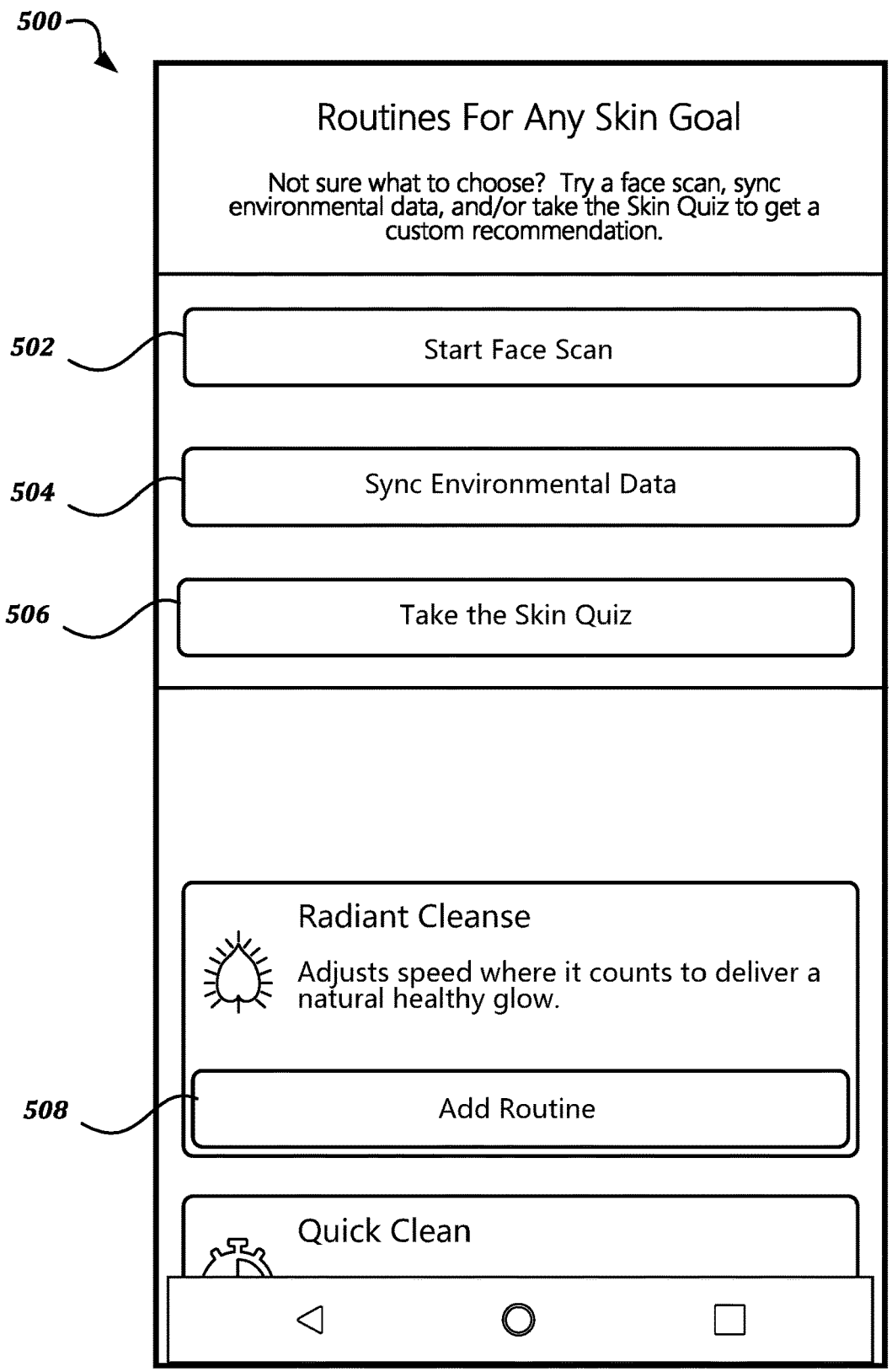
FIG. 5 is a screenshot diagram of an illustrative skin-care routine selection screen, in accordance with a described embodiment.

FIG. 5 depicts a screenshot of an illustrative skin-care routine selection screen 500, in accordance with a described embodiment. The screen 500 includes options for selecting a pre-defined care routine or, if the user so desires, for generating a custom care routine. The screen 500 includes illustrative UI elements in the form of a button 502 to initiate a process to capture one or more face images or scans, a button 504 to initiate a process to obtain environmental data, and a button 506 to obtain user data, in the form of a questionnaire or "skin quiz." In an embodiment, upon activation of the button 502, a user is directed to take a self-portrait or a series of such pictures, which are analyzed by face scan software to generate a digital model of the user's face that includes skin characteristics and features. In an embodiment, the characteristics and features include lip and eye edges, skin features including blemishes, areas of hyper-pigmentation, texture, or wrinkles, or other features or combinations thereof. The home screen includes an additional button 508 that may be used to add a pre-defined skin care routine.

Figure 6A:
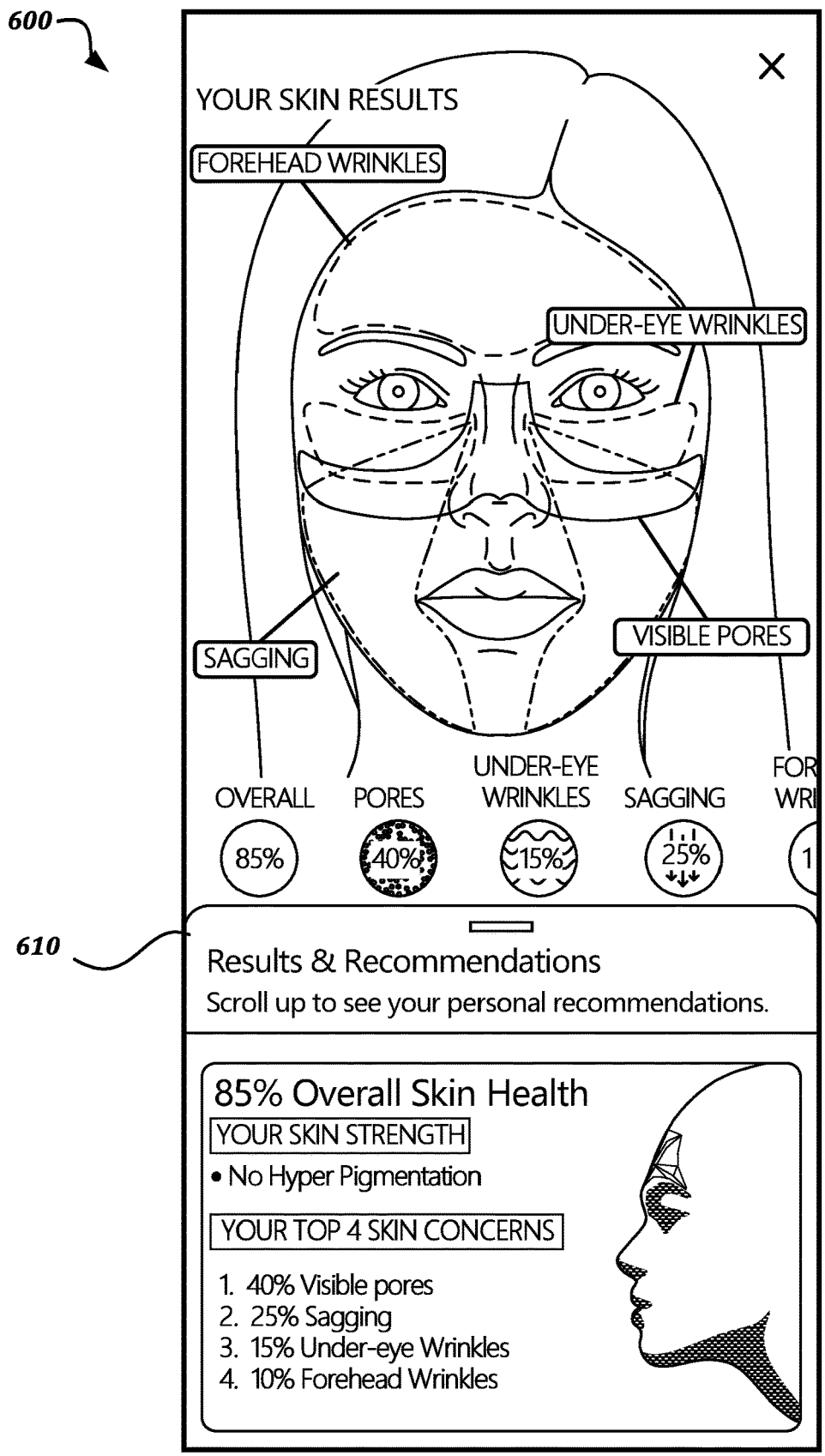
FIGS. 6A and 6B are screenshot diagrams of illustrative face scan analysis screens, in accordance with a described embodiment.
Figure 6B:
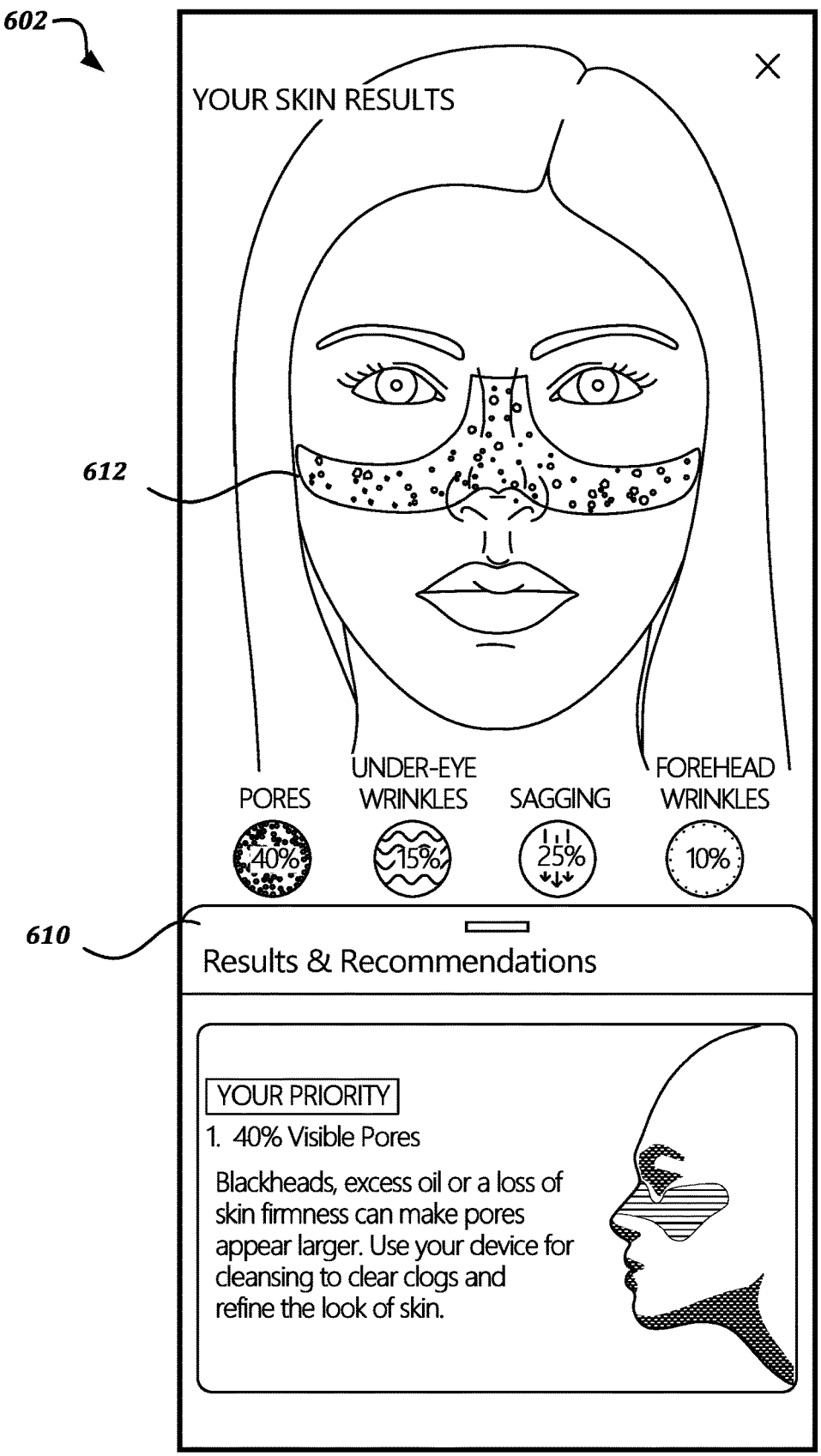

FIGS. 6A and 6B depict screenshots of illustrative face scan analysis screens, which may be presented to a user after generation of a face scan, in accordance with a described embodiment. As mentioned above, the model of the users face may include detected facial features such as lip and eye edges, as well as skin features such as wrinkles, texture, and blemishes. In FIG. 6A, the screen 600 includes a self-portrait image of the user with graphical overlays depicting areas of interest or concern on the user's face, including detected areas of wrinkles, sagging, and visible pores. These overlays are drawn based on the results of the face scan. The example shown in screen 600 also includes skin scores, including an overall condition score for the user's face, as well as sub-scores relating to visible pores, wrinkles, sagging, and pigmentation, and labeled graphical overlays corresponding to detected problem areas. The screen includes a scrollable tab 610 which allows a user to scroll up to see personal recommendations for skin care. In FIG. 6B, the screen 602 shows the tab 610 in a scrolled-up position, revealing additional feedback relating to a skin concern. In addition, the region in which this concern is most prominent is displayed in the graphic overlay 612, which is generated based on the face scan.

Figure 7:
Figure 8:
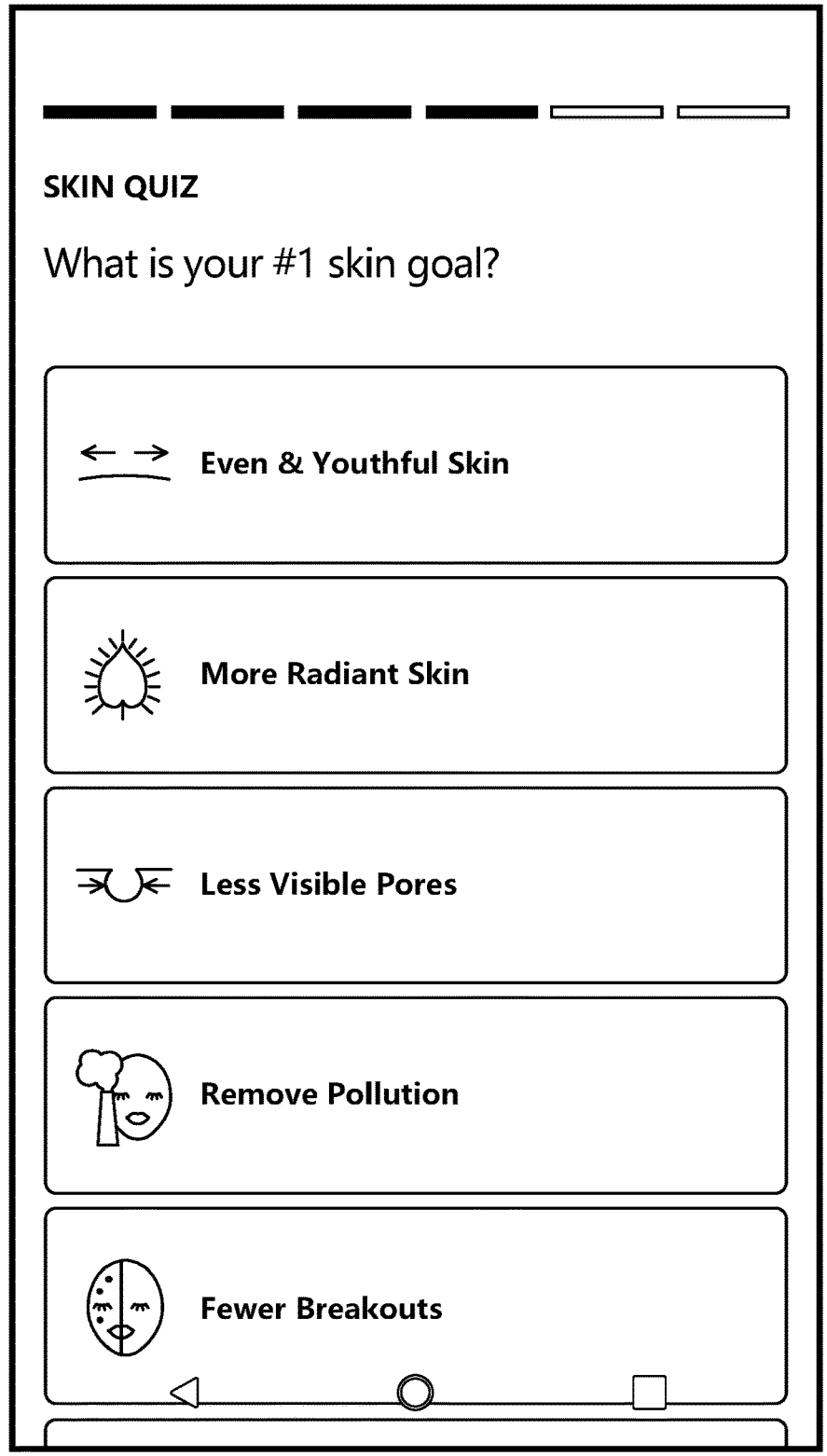

FIGS. 7-9 depicts screenshots of illustrative questionnaire screens 700, 800, and 900, in accordance with a described embodiment. The illustrative screens include UI elements that are used to collect user data on topics such as skin type, skin care goals, and facial areas that may be of particular concern to the user. Other UI elements may be used to collect information on similar or different topics.

Figure 10:
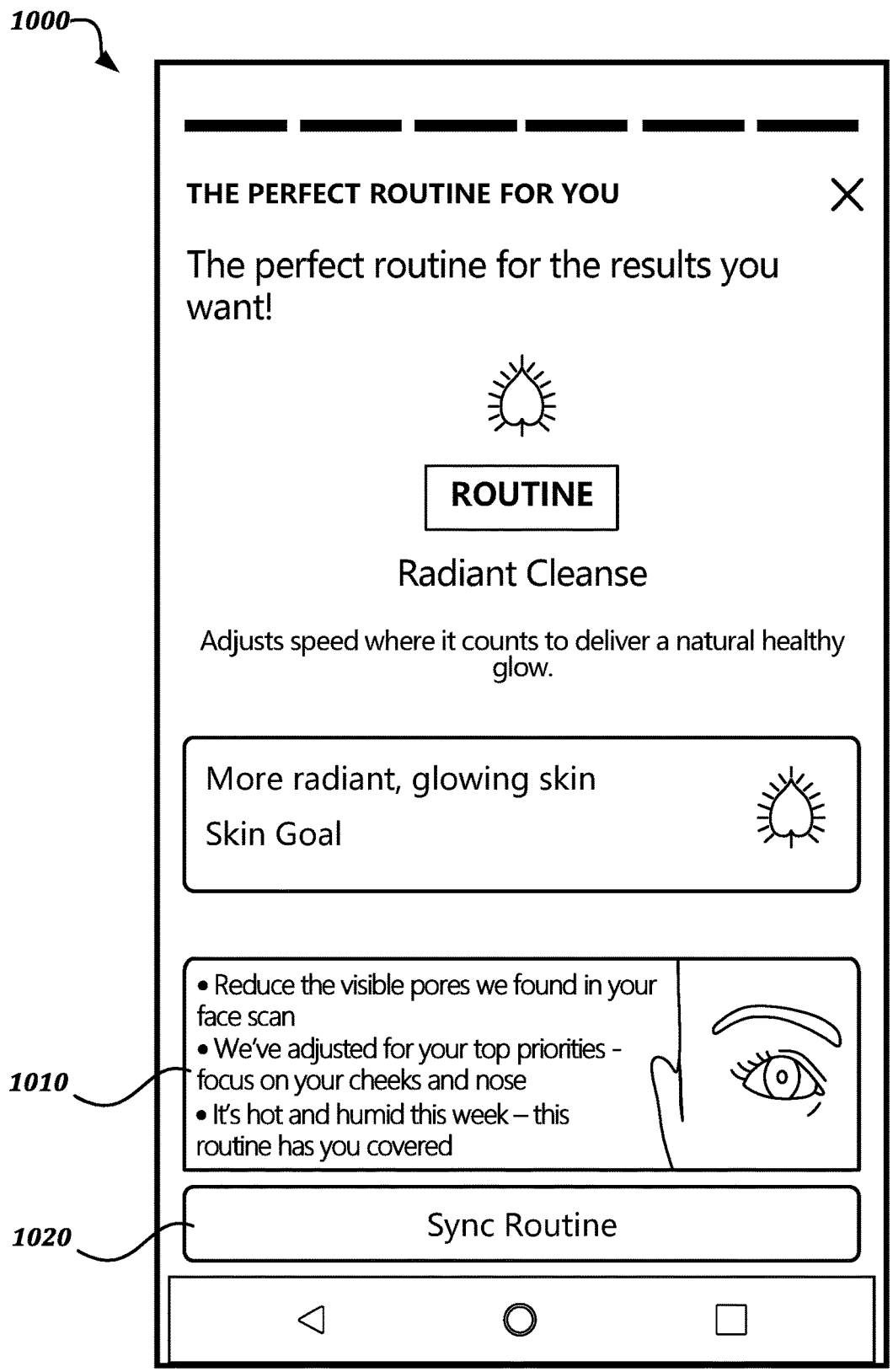
FIG. 10 is a screenshot diagram of an illustrative result screen in which a skin-care routine has been generated based on a face scan and other inputs, in accordance with a described embodiment.

FIG. 10 depicts a screenshot of an illustrative result screen in which a skin-care routine has been generated based on a face scan and other inputs, in accordance with a described embodiment. In the result screen 1000, the user is informed via UI element 1010 that a routine has been generated based on the face scan, environmental data, and user data. For example, the routine may include steps designed to reduce visible pores identified in the face scan, to use a cleanser appropriate for hot, humid weather identified in the environmental data, and longer duration of cleansing for user-identified focus areas. The user is given the option, via button 1020, to add this new routine to their skin care device. In an embodiment, activation of the button 1020 causes data and program instructions for performing the new routine to be transmitted from the client computing device 104 to the skin care device 102 via Bluetooth. Alternatively, data and program instructions corresponding to the generated skin-care routine can be transmitted, stored, or implemented in some other way.

Figure 11:
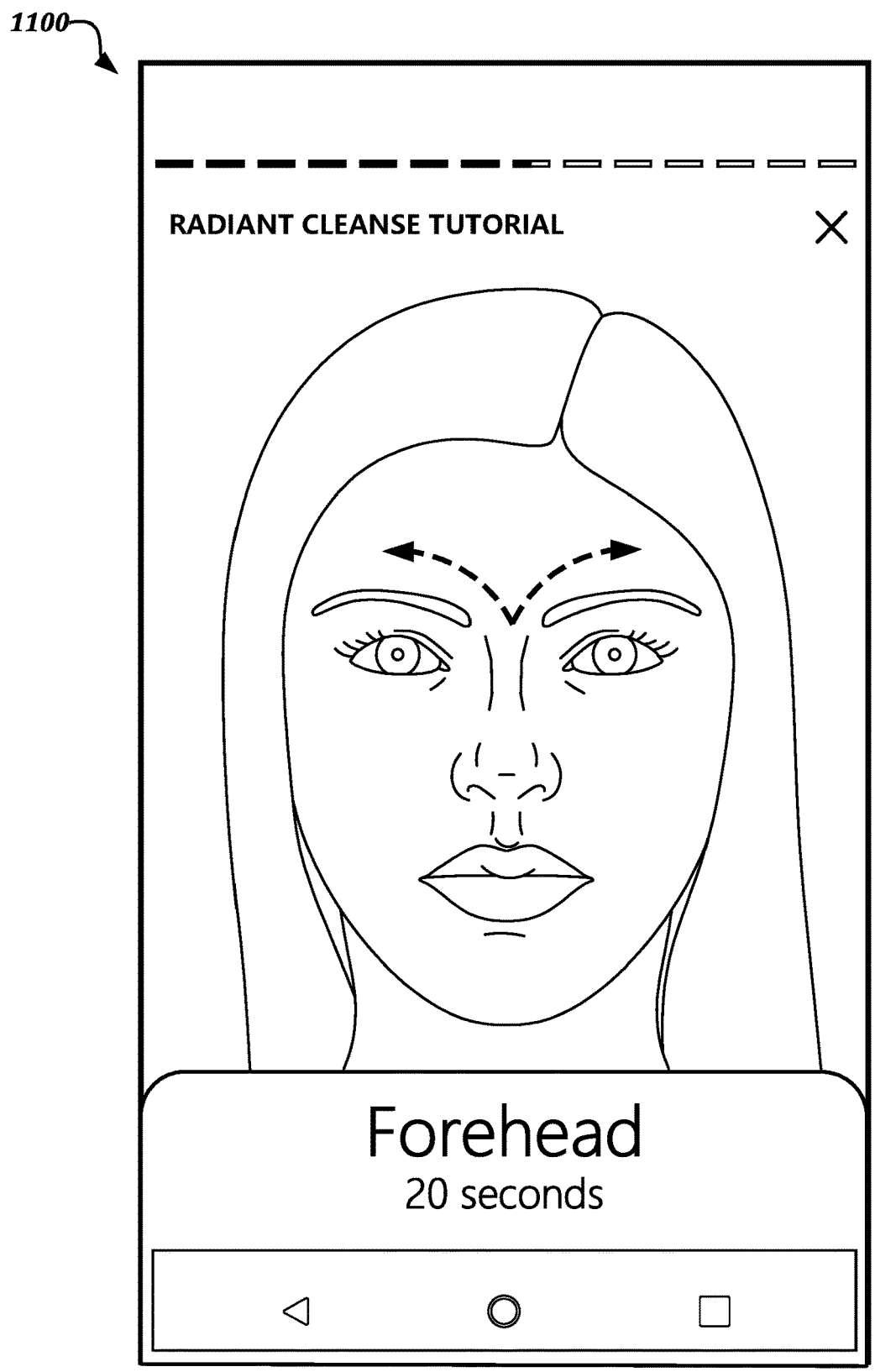
FIG. 11 is a screenshot diagram of an illustrative skin care routine tutorial screen, in accordance with a described embodiment.

FIG. 11 depicts a screenshot of an illustrative skin care routine tutorial screen 1100, in accordance with a described embodiment. In the tutorial screen 1100, the UI provides graphical animations that are overlaid on a self-portrait image and show, for example, paths to use for cleansing steps, such as the forehead cleansing step illustrated in screen 1100. In an embodiment, correct placement of the graphical animation relative to the self-portrait image is guided by the model that was previously generated based on the face scan.

Figure 12:
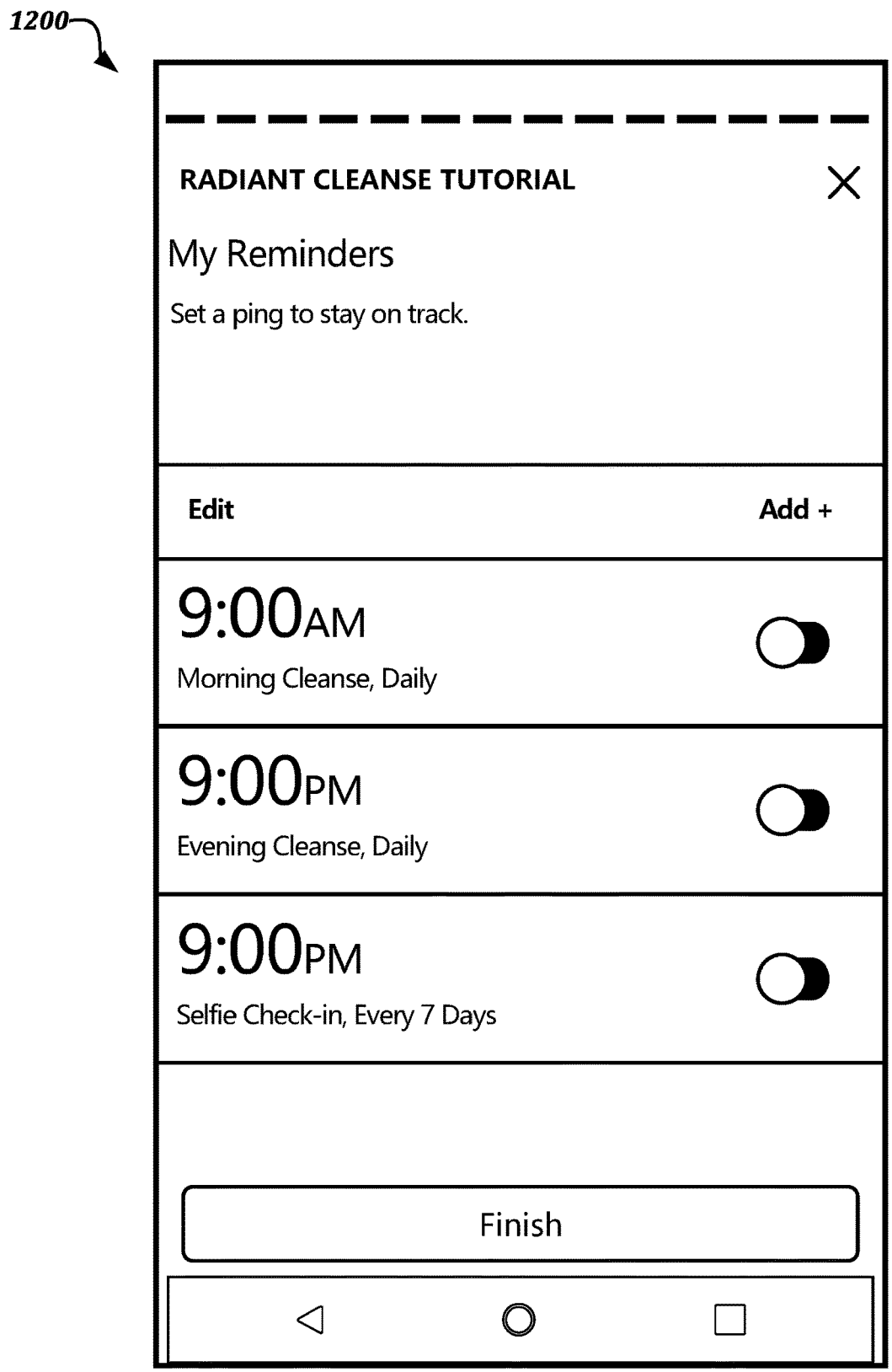
FIG. 12 is a screenshot diagram of an illustrative user preference screen, in accordance with a described embodiment.

FIG. 12 depicts a screenshot of an illustrative user preference screen 1200, in accordance with a described embodiment. The screen 1200 includes an example of how the UI can be designed to not only set user preferences, such as reminders to follow a routine, but to provide opportunities to update previously generated routines with new face scans or other data. The screen 1200 includes a reminder for a "selfie check-in every 7 days." This can be used to remind a user to record a new face scan every 7 days (or any other desired interval) and subsequently update a previously generated routine, if appropriate. In addition to the features depicted in FIG. 12, other user preferences (e.g., device settings, sound or voice settings, haptic feedback settings, visual UI settings, etc.) also can be set using similar or different UI elements.

In an embodiment, the computer-guided care routine comprises a plurality of stages, and the step of generating (e.g., creating or updating) the computer-guided care routine includes selecting from among available options for one or more of the stages based on a combination of data including a digital scan of the user's face and other user data (e.g., user preferences, device usage patterns, questionnaire/survey answers, etc.) along with environmental data. In an embodiment, these selections are further based on selection criteria such as characteristics of the skin care device (e.g., available brush heads, available brush head speeds), previous outcomes, time of day, day of week, day of year, or other selection criteria, or a combination thereof.

Figure 13:
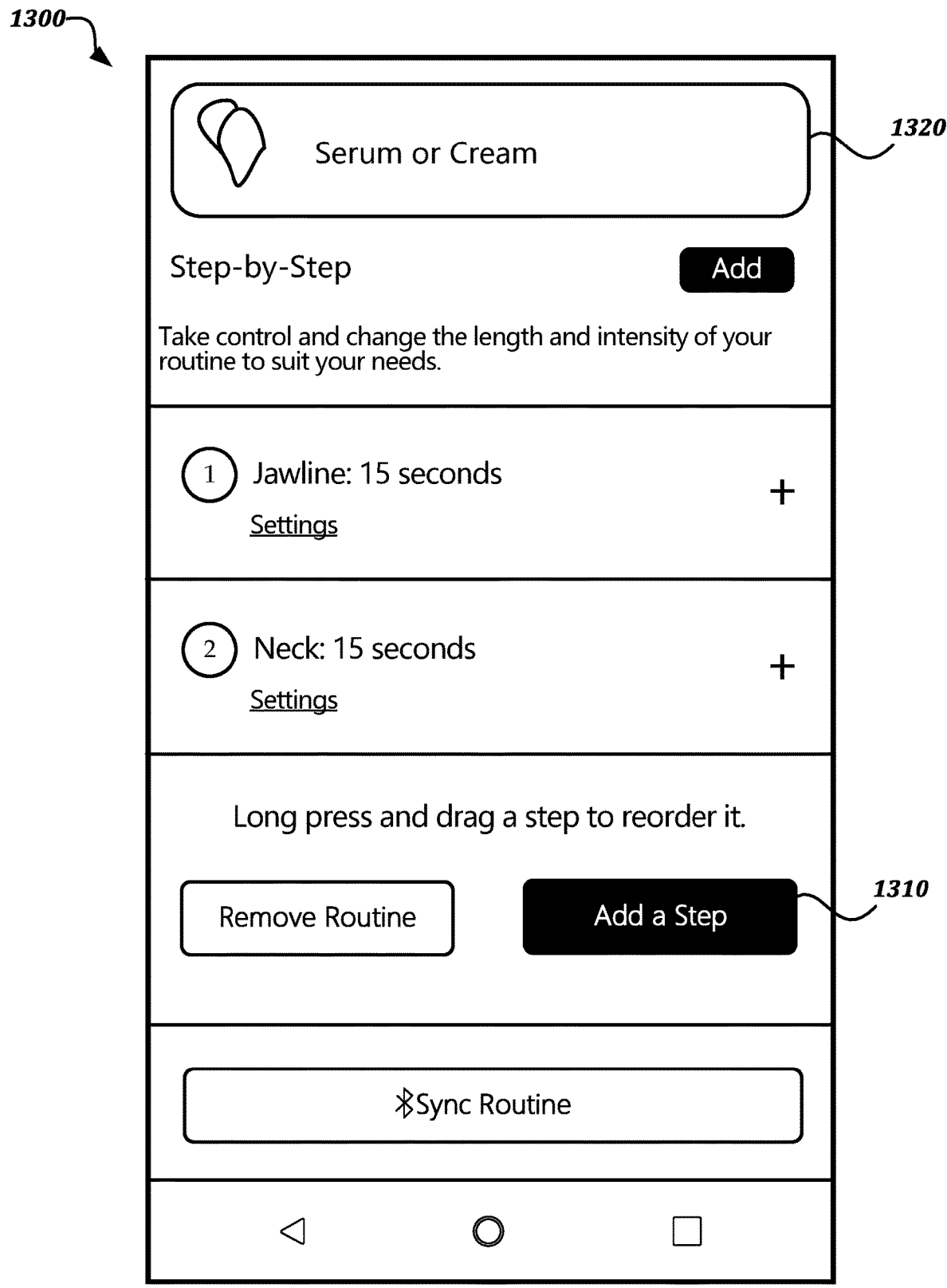
FIGS. 13 and 14 are screenshot diagrams of illustrative skin care routine editing screens, in accordance with a described embodiment.
Figure 14:
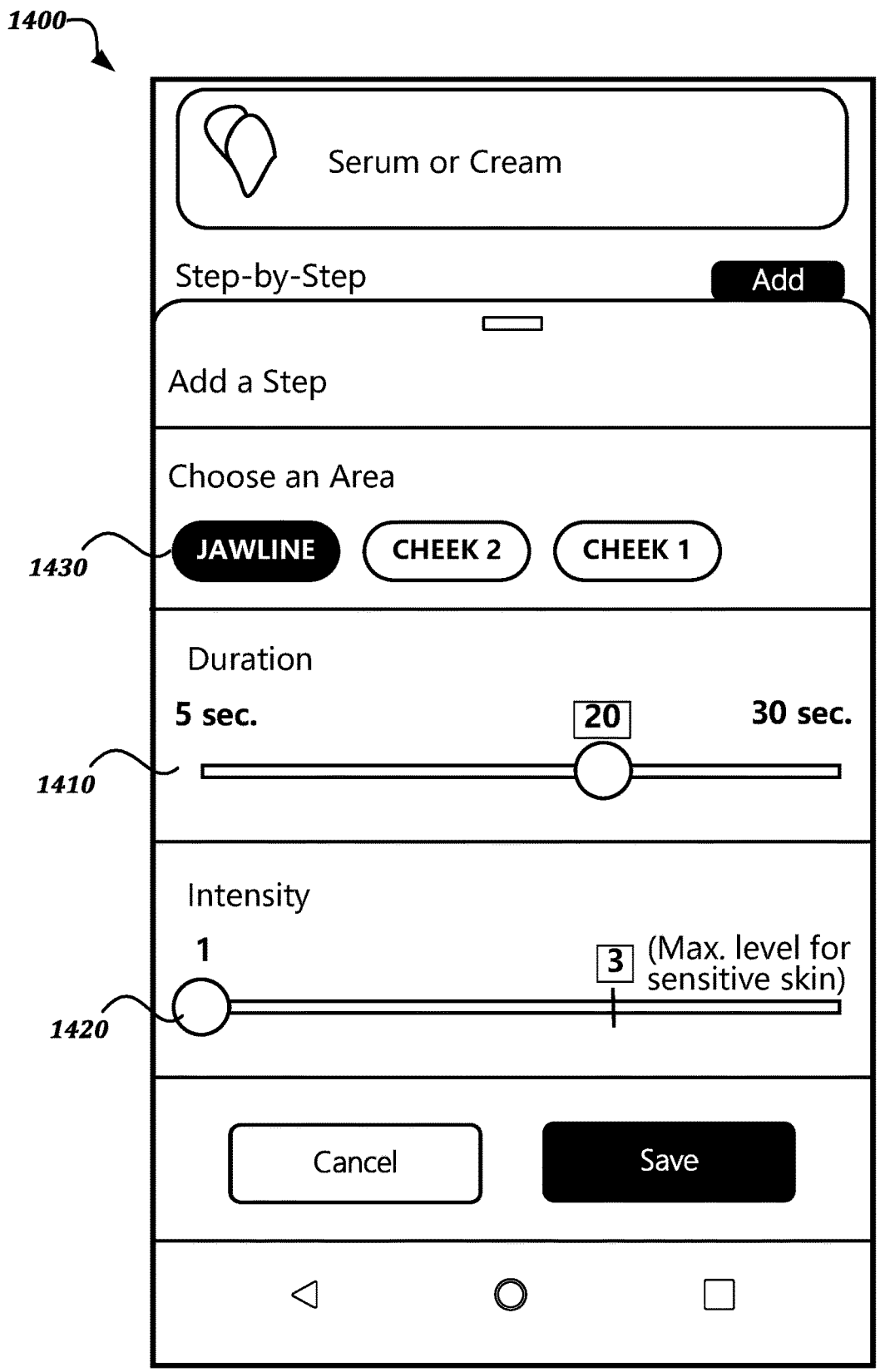

FIG. 13 depicts a screenshot of an illustrative skin care routine editing screen 1300, in accordance with a described embodiment. The screen 1300 includes further examples of how the UI can be designed to update previously generated routines. The screen 1300 includes UI elements showing current steps in a routine (jawline and neck cleansing steps) along with a button element 1310 configured to allow a user to add a step to the routine, as well as a button element 1320 configured to allow a user to view and/or modify a serum or cream to be used in the routine. In an embodiment, activation of the button 1310 leads to a further routine editing screen 1400, as shown in FIG. 14. In the illustrative screen 1400, the UI includes slider elements 1410, 1420 that allow a user to select parameters (e.g., intensity and duration) for a step to be added to a routine, as well as a button element 1430 that allows a user to select desired location (e.g., jawline, cheek, etc.) for the step to be added.

In an embodiment, parameters for steps to be added depend on data that has been previously collected. In an illustrative scenario, a user has previously indicated that she has sensitive skin, and the user's face scan indicates a problem area that may benefit from a longer duration of treatment. In the context of FIG. 14, this scenario involves a default value for the new step being set at a minimum intensity level ("1"), and a maximum value ("3") of the slider element 1420 is reduced to avoid intensity levels that are not appropriate for sensitive skin. On the other hand, the slider element 1410 is set at a default duration (e.g., 20 sec.) that is appropriate for a problem area identified in the face scan.

Figure 15:
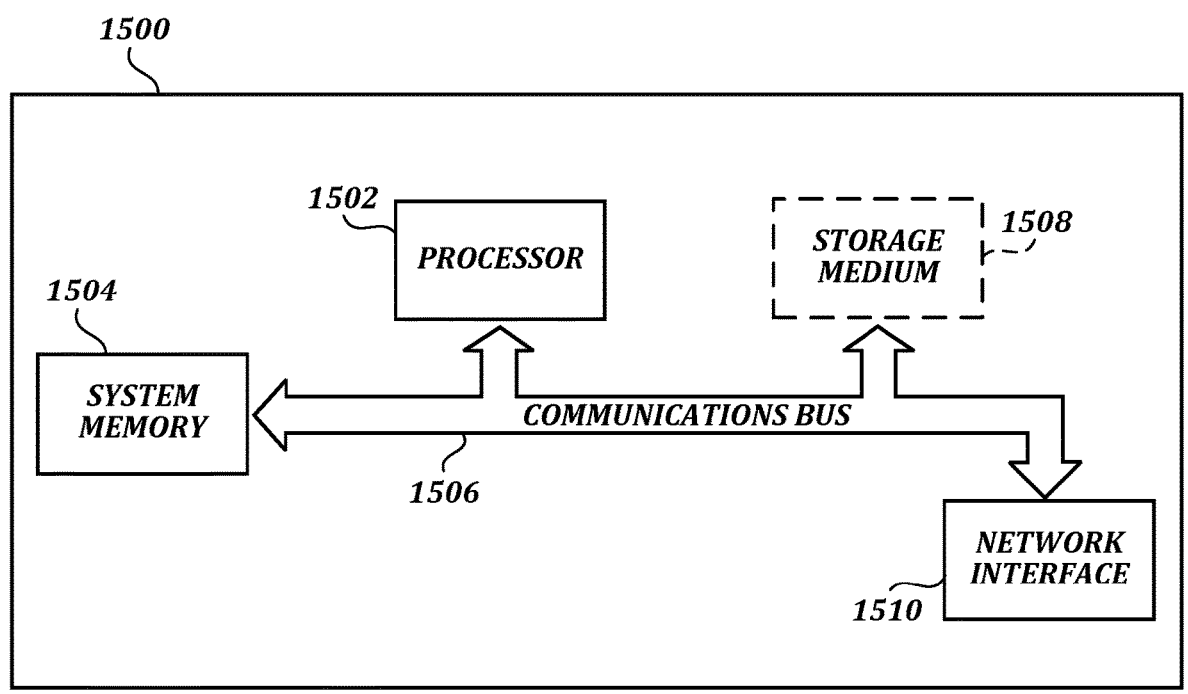
FIG. 15 is a block diagram that illustrates aspects of an exemplary computing device appropriate for use with embodiments of the present disclosure.

FIG. 15 is a block diagram that illustrates aspects of an exemplary computing device 1500 appropriate for use with embodiments of the present disclosure. While FIG. 15 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 1500 may be any one of any number of currently available or yet to be developed devices.

In its most basic configuration, the computing device 1500 includes at least one processor 1502 and a system memory 1504 connected by a communication bus 1506. Depending on the exact configuration and type of device, the system memory 1504 may be volatile or nonvolatile memory, such as read only memory ("ROM"), random access memory ("RAM"), EEPROM, flash memory, or similar memory technology. Those of ordinary skill in the art and others will recognize that system memory 1504 typically stores data and/or program modules that are immediately accessible to and/or currently being operated on by the processor 1502. In this regard, the processor 1502 may serve as a computational center of the computing device 1500 by supporting the execution of instructions.

As further illustrated in FIG. 15, the computing device 1500 may include a network interface 1510 comprising one or more components for communicating with other devices over a network. Embodiments of the present disclosure may access basic services that utilize the network interface 1510 to perform communications using common network protocols. The network interface 1510 may also include a wireless network interface configured to communicate via one or more wireless communication protocols, such as WiFi, 2G, 3G, LTE, 5G, WiMAX, Bluetooth, and/or the like.

In the exemplary embodiment depicted in FIG. 15, the computing device 1500 also includes a storage medium 1508. However, services may be accessed using a computing device that does not include means for persisting data to a local storage medium. Therefore, the storage medium 1508 depicted in FIG. 15 is represented with a dashed line to indicate that the storage medium 1508 is optional. In any event, the storage medium 1508 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 1504 and storage medium 1508 depicted in FIG. 15 are merely examples of computer-readable media. In an embodiment, computer-readable media are used to store data for use by programs.

Suitable implementations of computing devices that include a processor 1502, system memory 1504, communication bus 1506, storage medium 1508, and network interface 1510 are known and commercially available. For ease of illustration and because it is not important for an understanding of the claimed subject matter, FIG. 15 does not show some of the typical components of many computing devices. In this regard, the computing device 1500 may include input devices, such as a keyboard, keypad, mouse, microphone, touch input device, touch screen, tablet, and/or the like. Such input devices may be coupled to the computing device 1500 by wired or wireless connections including RF (radio frequency), infrared, serial, parallel, Bluetooth®, USB, or other suitable connections protocols using wireless or physical connections. Similarly, the computing device 1500 may also include output devices such as a display, speakers, printer, etc. Since these devices are well known in the art, they are not illustrated or described further herein.

EXTENSIONS AND ALTERNATIVES

Many alternatives to the systems and devices described herein are possible. For example, individual modules or subsystems may be separated into additional modules or subsystems or combined into fewer modules or subsystems. As another example, modules or subsystems may be omitted or supplemented with other modules or subsystems. As another example, functions that are indicated as being performed by a particular device, module, or subsystem may instead be performed by one or more other devices, modules, or subsystems. Although some examples in the present disclosure include descriptions of devices comprising specific hardware components in specific arrangements, techniques and tools described herein may be modified to accommodate different hardware components, combinations, or arrangements. Further, although some examples in the present disclosure include descriptions of specific usage scenarios, techniques and tools described herein may be modified to accommodate different usage scenarios. Functionality that is described as being implemented in software may instead be implemented in hardware, or vice versa.

Many alternatives to the techniques described herein are possible. For example, processing stages in the various techniques may be separated into additional stages or combined into fewer stages. As another example, processing stages in the various techniques may be omitted or supplemented with other techniques or processing stages. As another example, processing stages that are described as occurring in a particular order may instead occur in a different order. As another example, processing stages that are described as being performed in a series of steps may instead be handled in a parallel fashion, with multiple modules or software processes concurrently handling one or more of the illustrated processing stages.

Many alternatives to the user interfaces described herein are possible. In practice, the user interfaces described herein may be implemented as separate user interfaces or as different states of the same user interface, and the different states can be presented in response to different events, e.g., user input events. The user interfaces can be customized for different devices, input and output capabilities, and the like. For example, the user interfaces can be presented in different ways depending on display size, display orientation, whether the device is a mobile device, etc. The information and user interface elements shown in the user interfaces can be modified, supplemented, or replaced with other elements in various possible implementations. For example, various combinations of graphical user interface elements including text boxes, sliders, drop-down menus, radio buttons, soft buttons, etc., or any other user interface elements, including hardware elements such as buttons, switches, scroll wheels, microphones, cameras, etc., may be used to accept user input in various forms. As another example, the user interface elements that are used in a particular implementation or configuration may depend on whether a device has particular input and/or output capabilities (e.g., a touchscreen). Information and user interface elements can be presented in different spatial, logical, and temporal arrangements in various possible implementations. For example, information or user interface elements depicted as being presented simultaneously on a single page or screen may also be presented at different times, on different pages or screens, etc. As another example, some information or user interface elements may be presented conditionally depending on previous input, user preferences, or the like.

While illustrative embodiments have been illustrated and described, it will be appreciated that various changes can be made therein without departing from the spirit and scope of the invention.

The embodiments of the invention in which an exclusive property or privilege is claimed are defined as follows:

1. A non-transitory computer-readable medium having stored thereon instructions configured to, when executed by one or more computing devices of a computer system, cause the computer system to perform operations comprising:
    obtaining a digital model of a face of a live human subject, wherein the digital model includes 3D topology and texture information;
    obtaining user data associated with the live human subject;
    detecting a plurality of skin features in the digital model, wherein the detected skin features include hyper-pigmentation, visible pores, and wrinkles;
    displaying a self-portrait image of the live human subject with a plurality of graphical overlays based on the 3D topology and texture information, wherein the graphical overlays depict boundaries of detected skin feature areas including a hyper-pigmentation area, a visible pores area, and a wrinkles area in which the corresponding skin features are detected to be present, and wherein two or more of the graphical overlays depicting the boundaries of the detected skin feature areas at least partially overlap each other on the displayed self-portrait image; and
    generating a computer-guided personal care routine based at least in part on the digital model of the face of the live human subject, the detected skin features, and the user data.

2. The computer-readable medium of claim 1, wherein the computer-guided personal care routine comprises one or more operational settings for a computer-controlled skin care device.

3. The computer-readable medium of claim 1, the operations further comprising obtaining environmental data associated with an environment of the live human subject, wherein the computer-guided personal care routine is further based on the environmental data.

4. The computer-readable medium of claim 3, wherein the environmental data includes temperature data, humidity data, pollution data, or UV radiation data, or a combination thereof.

5. The computer-readable medium of claim 3, wherein the environmental data is obtained from a remote computer system or one or more environmental sensors or a combination thereof.

6. The computer-readable medium of claim 1, wherein one or more prompts associated with the computer-guided personal care routine are configured to be presented in a user interface.

7. The computer-readable medium of claim 1, wherein the user data includes user preference data.

8. The computer-readable medium of claim 7, wherein the user preference data comprises an age target.

9. The computer-readable medium of claim 1, the operations further comprising:
    obtaining user feedback relating to the computer-guided personal care routine via a user interface; and
    modifying the computer-guided personal care routine based at least in part on the user feedback.

10. The computer-readable medium of claim 1, wherein the computer-guided personal care routine includes a product recommendation or a self-care recommendation associated with a skin care routine.

11. The computer-readable medium of claim 1, wherein obtaining the digital model of the face of the live human subject comprises processing a depth image of the face captured by a client computing device.

12. A computer-implemented method comprising:
obtaining, by a computing device, a digital model of a face of a live human subject, wherein the digital model includes 3D topology and texture information;
obtaining, by the computing device, user data associated with the live human subject;
detecting, by the computing device, a plurality of skin features in the digital model, wherein the detected skin features include hyper-pigmentation, visible pores, and wrinkles;
generating, by the computing device, a self-portrait image of the live human subject with a plurality of graphical overlays based on the 3D topology and texture information, wherein the graphical overlays depict boundaries of detected skin feature areas including a hyper-pigmentation area, a visible pores area, and a wrinkles area in which the corresponding skin features are detected to be present, and wherein two or more of the graphical overlays depicting the boundaries of the detected skin feature areas at least partially overlap each other on the self-portrait image; and
generating, by the computing device, a computer-guided skin care routine based at least in part on the digital model of the face of the live human subject and the user data.

13. The computer-implemented method of claim 12, wherein the computer-guided skin care routine includes one or more operational settings for a computer-controlled skin care device, the method further comprising configuring or controlling the computer-controlled skin care device using the one or more operational settings.

14. The computer-implemented method of claim 12 further comprising obtaining environmental data associated with an environment of the live human subject, wherein the computer-guided skin care routine is further based on the environmental data.

15. The computer-implemented method of claim 14, wherein the environmental data includes temperature data, humidity data, pollution data, UV radiation data, or a combination thereof.

16. The computer-implemented method of claim 12 further comprising modifying the computer-guided skin care routine based at least in part on input received via a user interface.

17. The computer-implemented method of claim 12, wherein obtaining the digital model of the face of the live human subject comprises processing a depth image of the face captured by a client computing device.

18. A computer system comprising a processor and a non-transitory computer-readable medium having stored thereon instructions configured to, when executed by one or more computing devices of the computer system, cause the computer system to perform operations comprising:
obtaining a digital model of a face of a live human subject, wherein the digital model includes 3D topology and texture information;
obtaining user data associated with the live human subject;
detecting a plurality of skin features in the digital model, wherein the detected skin features include hyper-pigmentation, visible pores, and wrinkles;
generating a self-portrait image of the live human subject with a plurality of graphical overlays based on the 3D topology and texture information, wherein the graphical overlays depict boundaries of detected skin feature areas including a hyper-pigmentation area, a visible pores area, and a wrinkles area in which the corresponding skin features are detected to be present, and wherein two or more of the graphical overlays depicting the boundaries of the detected skin feature areas at least partially overlap each other on the self-portrait image; and
generating a computer-guided skin care routine based at least in part on the digital model of the face of the live human subject and the user data.

19. The computer system of claim 18, the operations further comprising obtaining environmental data associated with an environment of the live human subject, wherein the computer-guided skin care routine is further based on the environmental data.

20. The computer system of claim 18 further comprising a camera configured to capture one or more digital images on which the digital model is based, wherein the one or more digital images comprise a depth image.

* * * * *